(12) United States Patent
Orr

(10) Patent No.: US 8,357,118 B2
(45) Date of Patent: Jan. 22, 2013

(54) BALLOON CATHETERS HAVING A PLURALITY OF NEEDLES FOR THE INJECTION OF ONE OR MORE THERAPEUTIC AGENTS

(75) Inventor: David E. Orr, Piedmont, SC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/059,856

(22) PCT Filed: Aug. 24, 2009

(86) PCT No.: PCT/US2009/004811
§ 371 (c)(1),
(2), (4) Date: Mar. 23, 2011

(87) PCT Pub. No.: WO2010/024871
PCT Pub. Date: Mar. 4, 2010

(65) Prior Publication Data
US 2011/0166516 A1    Jul. 7, 2011

Related U.S. Application Data

(60) Provisional application No. 61/091,894, filed on Aug. 26, 2008.

(51) Int. Cl.
*A61M 29/00* (2006.01)
(52) U.S. Cl. ............ 604/103.01; 604/96.01; 604/103.08
(58) Field of Classification Search ............... 604/96.01, 604/103.01, 103.02, 103.08
See application file for complete search history.

(56) References Cited

U.S. PATENT DOCUMENTS

| 4,641,653 A | 2/1987 | Rockey |
| 4,681,564 A | 7/1987 | Landreneau |
| 4,994,033 A | 2/1991 | Shockey et al. |
| 5,423,851 A * | 6/1995 | Samuels ................ 606/198 |
| 5,558,642 A | 9/1996 | Schweich, Jr. et al. |

(Continued)

FOREIGN PATENT DOCUMENTS

| EP | 1230944 | 8/2002 |
| EP | 1825824 | 8/2007 |

(Continued)

OTHER PUBLICATIONS

International Search Report and Written Opinion for PCT/US2009/004811 dated Oct. 22, 2009, 18 pgs.

(Continued)

*Primary Examiner* — Laura Bouchelle
(74) *Attorney, Agent, or Firm* — Brinks Hofer Gilson & Lione (57) ABSTRACT

There are disclosed apparatus and methods for treating tissue by delivering at least one therapeutic agent into the tissue. In one embodiment, the apparatus comprises a catheter (30, 40) and a balloon member (150) disposed on a distal region of the catheter. A plurality of pockets (164) are disposed on the balloon member (150), and a plurality of needles (180) are associated with each of the plurality of pockets. The plurality of needles (180) are configured to engage tissue when the balloon (150) is in the inflated state, and further are configured to disperse a therapeutic agent from an associated pocket (164) into the tissue when the balloon (150) is in the inflated state. A first needle (180a) of the plurality of needles may comprise a length that is different than a second needle (180b), permitting the delivery of first and second therapeutic agents to different depths within the tissue.

14 Claims, 5 Drawing Sheets

U.S. PATENT DOCUMENTS

| | | |
|---|---|---|
| 5,985,307 A | 11/1999 | Hanson et al. |
| 6,048,332 A | 4/2000 | Duffy et al. |
| 6,210,392 B1 | 4/2001 | Vigil et al. |
| 6,544,221 B1 | 4/2003 | Kokish et al. |
| 6,695,830 B2 | 2/2004 | Vigil et al. |
| 6,764,461 B2 | 7/2004 | Mickley et al. |
| 6,945,957 B2 | 9/2005 | Freyman |
| 6,991,617 B2 | 1/2006 | Hektner et al. |
| 2001/0020151 A1* | 9/2001 | Reed et al. ............... 604/103.02 |
| 2004/0064093 A1* | 4/2004 | Hektner et al. .......... 604/103.01 |
| 2004/0064094 A1 | 4/2004 | Freyman |
| 2004/0073190 A1 | 4/2004 | Deem et al. |
| 2005/0273049 A1 | 12/2005 | Krulevitch et al. |
| 2005/0273075 A1 | 12/2005 | Krulevitch et al. |

FOREIGN PATENT DOCUMENTS

| | | |
|---|---|---|
| WO | WO02/43796 | 6/2002 |

OTHER PUBLICATIONS

Response to International Search Report and Written Opinion for PCT/US2009/004811 dated Jan. 4, 2010, 3 pgs.

International Preliminary Report on Patentability for PCT/US2009/004811 dated Aug. 24, 2010, 17 pgs.

* cited by examiner

BALLOON CATHETERS HAVING A PLURALITY OF NEEDLES FOR THE INJECTION OF ONE OR MORE THERAPEUTIC AGENTS

RELATED APPLICATIONS

The present patent document is a §371 filing based on PCT Application Ser. No. PCT/US2009/004811, filed Aug. 24, 2009 (and published as WO 2010/024871A1 on Mar. 4, 2010), designating the United States and published in English, which claims the benefit of the filing date under 35 U.S.C. §119(e) of Provisional U.S. Patent Application Ser. No. 61/091,894, filed Aug. 26, 2008. All of the foregoing applications are hereby incorporated by reference in their entirety.

TECHNICAL FIELD

The present invention relates to apparatus for treating tissue at a target site, and to a method of treating tissue at a target site. The preferred embodiment relates to a balloon catheter provided with a plurality of needles configured to deliver one or more therapeutic agents into the tissue.

BACKGROUND ART

There are several instances in which it may become desirable to introduce therapeutic agents into a human or animal body. For example, therapeutic drugs or bioactive materials may be introduced to achieve a biological effect. The biological effect may include an array of targeted results, such as inducing hemostasis, reducing restenosis likelihood, or treating cancerous tumors or other diseases.

Many of such therapeutic agents are injected using an intravenous (IV) technique and via oral medicine. While such techniques permit the general introduction of medicine, in many instances it may be desirable to provide localized or targeted delivery of therapeutic agents, which may allow for the guided and precise delivery of agents to selected target sites.

For example, localized delivery of therapeutic agents to a tumor may reduce the exposure of the therapeutic agents to normal, healthy tissues, which may reduce potentially harmful side effects. Similarly, therapeutic agents may be delivered locally to a diseased portion of a coronary vessel to reduce, halt or reverse the progression of a stenosis, or may be delivered to a diseased portion of the aorta in order to reduce, halt or reverse the progression of an abdominal aortic aneurysm.

Localized delivery of therapeutic agents has been performed using catheters and similar introducer devices. By way of example, a catheter may be advanced towards a target site within the patient, then the therapeutic agent may be injected through a lumen of the catheter to the target site. Typically, a syringe or similar device may be used to inject the therapeutic agent into the lumen of the catheter. The therapeutic agent then may exit through a port disposed in a lateral surface at the distal end of the catheter. Typical catheter systems that locally deliver a therapeutic agent are limited in that they may only deliver one therapeutic agent at a time into the tissue. Moreover, it may be difficult to deliver a therapeutic agent to different depths into the tissue, resulting in treatment of only a portion of the tissue, e.g., the intimal layer, with one type of therapeutic agent. If multiple therapeutic agents are desired, or one or more agents are intended to be delivered at different tissue depths, then multiple components may need to be sequentially removed and inserted to achieve this result.

DISCLOSURE OF THE INVENTION

The present invention seeks to provide improved treatment of tissue at a target site.

The present invention provides apparatus and methods for treating tissue by delivering at least one therapeutic agent into the tissue. In a first embodiment, the apparatus comprises an inner cannula and an outer cannula disposed substantially co-axially over the inner cannula to form a delivery channel therebetween. An inner balloon member is disposed on a distal region of the inner cannula, and an outer balloon member is disposed substantially over the inner balloon member. A plurality of pockets are disposed on the outer balloon member, or formed integrally with the balloon, and at least one needle is associated with at least one of the plurality of pockets. The inner balloon member is inflated to cause the plurality of needles to engage tissue, and a therapeutic agent is delivered through the plurality of needles, via the delivery channel and the plurality of pockets, to dispense the therapeutic agent into the tissue.

In another embodiment, the apparatus comprises a catheter, a balloon member, and a plurality of pockets disposed on the balloon member. A plurality of needles, associated with each of the plurality of pockets, are configured to engage tissue when the balloon is in the inflated state, and are further configured to disperse a therapeutic agent from an associated pocket into the tissue when the balloon is in the inflated state. A first needle may comprise a length that is different than a length of a second needle, thereby permitting the delivery of first and second therapeutic agents to different depths within the tissue.

In one embodiment, each of the plurality of pockets may be separate and discrete from another pocket, and a therapeutic agent is disposed individually within each of the plurality of pockets. Alternatively, each of the plurality of pockets may be placed in fluid communication with at least one other pocket. In the latter embodiment, a first series of pockets comprising needles having first lengths may be placed in fluid communication with one another, and a second series of pockets comprising needles having second lengths may be placed in fluid communication with one another. This allows a first therapeutic agent to be delivered through the first series of pockets to a first tissue depth, and a second therapeutic agent to be delivered through the second series of pockets to a second tissue depth.

Advantageously, one or more therapeutic agents may be locally delivered to a desired target site in a fast and efficient manner. Moreover, if multiple therapeutic agents are desired, different therapeutic agents may be delivered to different tissue locations and depths, without the need to remove and insert multiple different components.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

Embodiments of the present invention are described below, by way of example only, with reference to the accompanying drawings in which.

DETAILED DESCRIPTION OF THE PREFERRED EMBODIMENTS

In the present application, the term "proximal" refers to a direction that is generally toward a physician during a medical procedure, while the term "distal" refers to a direction that is generally toward a target site within a patient's anatomy during a medical procedure.

Figure 1:
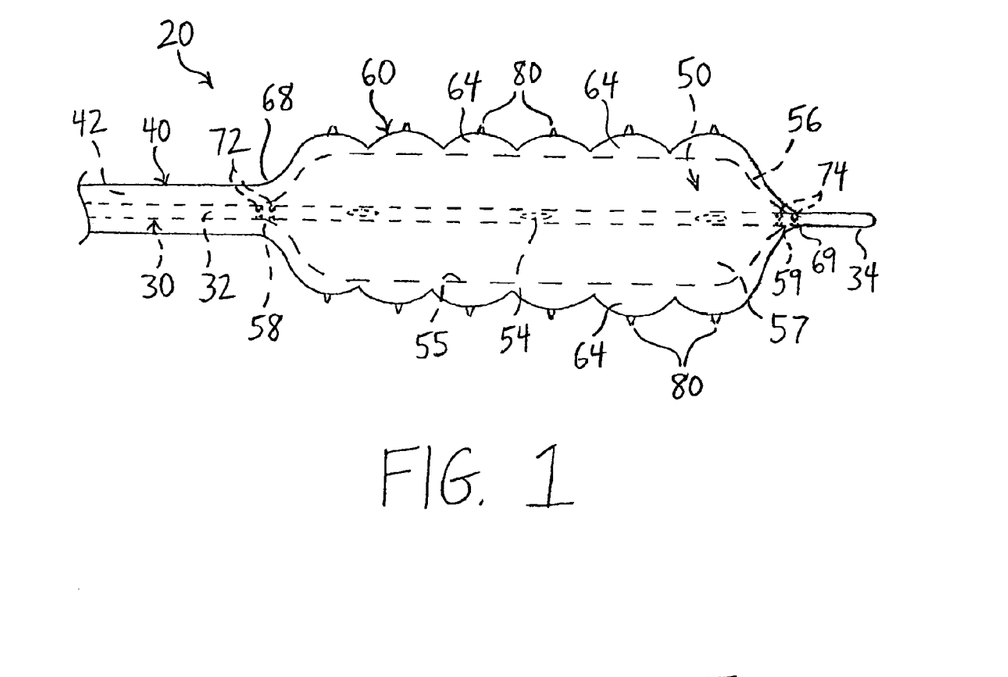
FIG. 1 is a side view of an apparatus for delivering at least one therapeutic agent according to a first embodiment.
Figure 2:
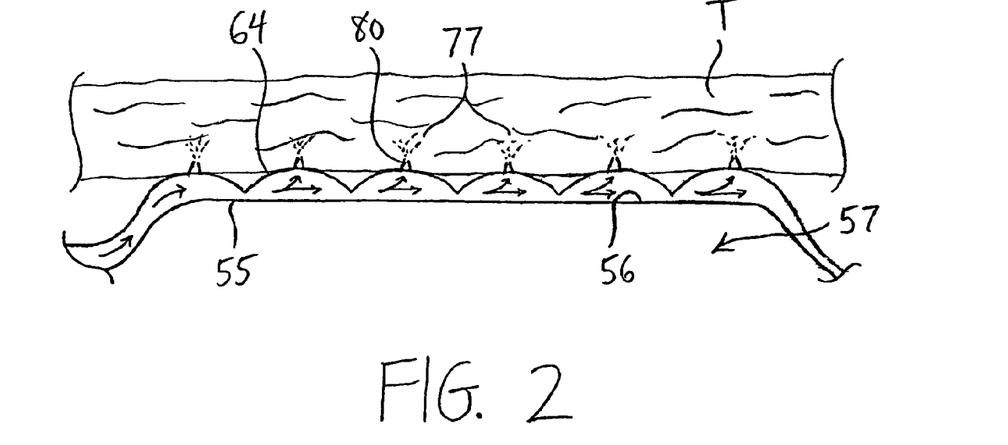
FIG. 2 is an enlarged side-sectional view of a portion of the apparatus of FIG. 1 engaging tissue.

Referring now to FIGS. 1-2, a first embodiment of an apparatus for delivering at least one therapeutic agent to treat a medical condition, such as a stenosis or an aneurysm, is described. The apparatus 20 comprises an inner cannula 30 and an outer cannula 40, each having proximal and distal regions. The inner cannula 30 has an inflation lumen 32 formed therein, as shown in FIG. 1. The outer cannula 40 is substantially co-axially disposed around the inner cannula 30, thereby forming a delivery channel 42 that may comprise an annular shape.

Figure 8:
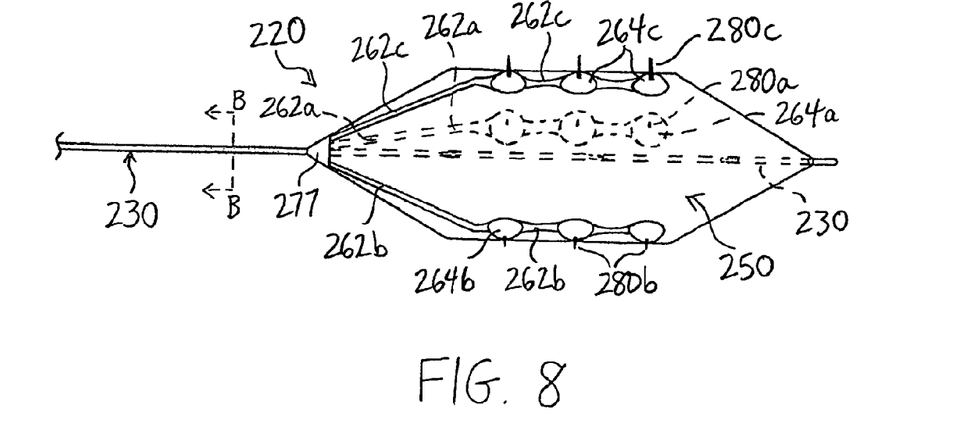
FIG. 8 is a side view of another embodiment of apparatus for delivering at least one therapeutic agent.
Figure 9:
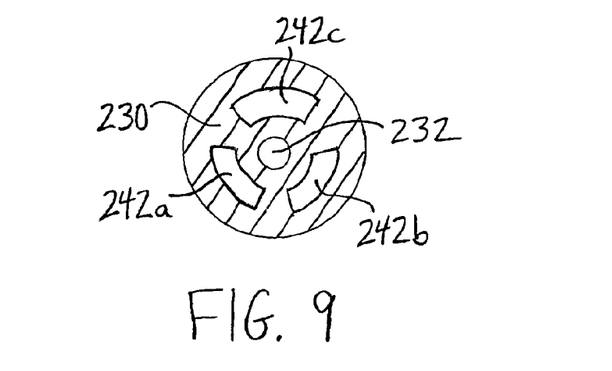
FIG. 9 is a cross-sectional view along line B-B of FIG. 8.
Figure 10:
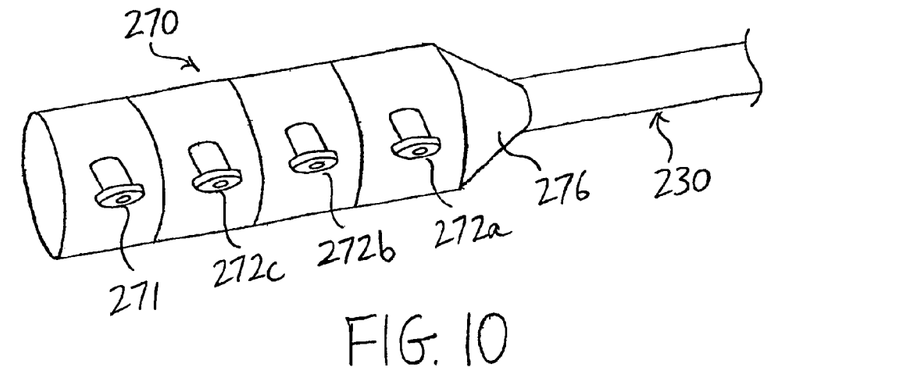
FIG. 10 is a perspective view of an exemplary proximal assembly that may be used in conjunction with the apparatus of FIG. 8.

The inner cannula 30 and the outer cannula 40 may comprise a flexible, tubular member that may be formed from one or more semi-rigid polymers. For example, the inner and outer cannulas 30 and 40 may be manufactured from polyurethane, polyethylene, tetrafluoroethylene, polytetrafluoroethylene, fluorinated ethylene propylene, nylon, PEBAX or the like. In the embodiment of FIGS. 1-2, while two separate inner and outer cannulas 30 and 40 are shown, it will be apparent that one integrally-formed catheter having multiple lumens may be employed, e.g., as shown in FIGS. 8-10 below, or alternatively, greater than two cannulas may be employed as part of a catheter assembly.

The apparatus 20 also includes an inner balloon member 50 and an outer balloon member 60 disposed substantially over the inner balloon member 50. The inner balloon member 50 has an inner surface 55 and an outer surface 56, and may be configured in a manner similar to a conventional interventional balloon, such as an angioplasty balloon. A proximal end of the inner balloon member 50 may be coupled to an outer surface of the inner cannula 30 at a proximal affixation point 58, while a distal end of the inner balloon member 50 may be coupled to an outer surface of the inner cannula 30 at a distal affixation point 59, as shown in FIG. 1. The inner balloon member 50 may be attached at these locations using any suitable adhesive, such as a biocompatible glue, and/or using heat-shrink tubing, heat bonding, laser bonding, welding, solvent bonding, one or more tie-down bands, or the like. Optionally, one or more proximal and distal radiopaque markers 72 and 74 may be provided in the vicinity of the proximal and distal affixation points 58 and 59, respectively.

At least one port 54 may be formed in the inner cannula 30 to provide fluid communication between the inflation lumen 32 of the inner cannula 30 and an interior space 57 of the inner balloon member 50. A proximal region of the inflation lumen 32 may be coupled to an inflation source. The provision of a fluid, such as saline, through the inflation lumen 32 causes inflation of the inner balloon member 50 to the inflated state, as shown in FIG. 1.

The outer balloon member 60 has a proximal end that is coupled to a distal end of the outer cannula 40 at a proximal affixation point 68, and the outer balloon member 60 also includes a distal end that is coupled to the inner cannula 30 at a distal affixation point 69, as shown in FIG. 1. The outer balloon member 60 also includes at least one pocket 64 having a needle 80 associated therewith for delivering a therapeutic agent. Preferably, multiple pockets 64 and associated needles 80 are provided, as shown in FIG. 1.

The plurality of pockets 64 and needles 80 may be disposed at multiple locations around the perimeter of the outer balloon member 60, and may be placed in fluid communication with the delivery channel 42, as shown in FIG. 1. As explained in further detail below, when one or more therapeutic agents are delivered through the annular space between the inner and outer cannulas 30 and 40, the therapeutic agents may be delivered into tissue via the plurality of needles 80.

The inner and outer balloon members 50 and 60 may be manufactured from a material including, but not limited to, PEBAX, nylon, Hytrel, Arnitel or other polymers, which may be suitable for use during an interventional procedure. Each of the pockets 64 may be integrally or externally coupled to an exterior surface of the outer balloon member 60. For example, the pockets 64 may be integrally formed into the outer balloon member 60 by molding the pockets 64 into a desired shape, e.g., a bulbous, circular, square, rectangular, oval, hexagonal or octagonal shape, or any other design.

Figure 3:
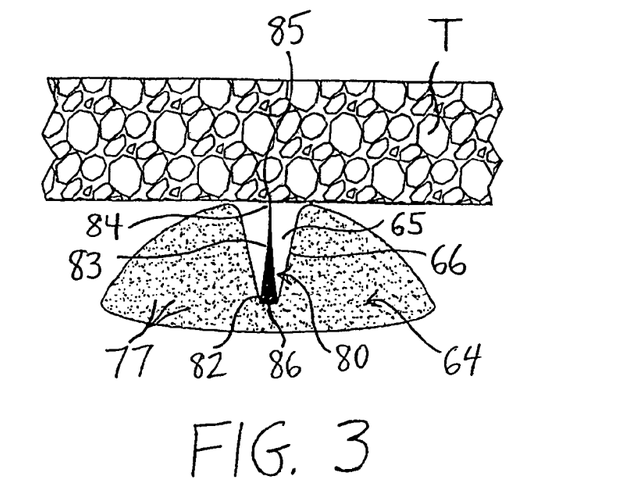
FIGS. 3-5 are side-sectional views illustrating an exemplary sequence of deployment of a pocket and an associated needle.
Figure 4:
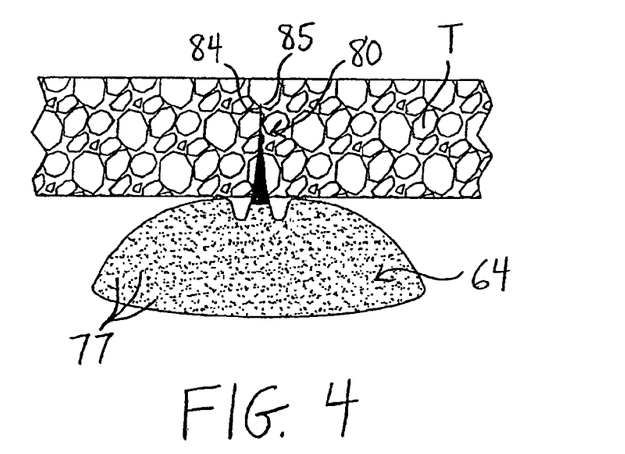
Figure 5:
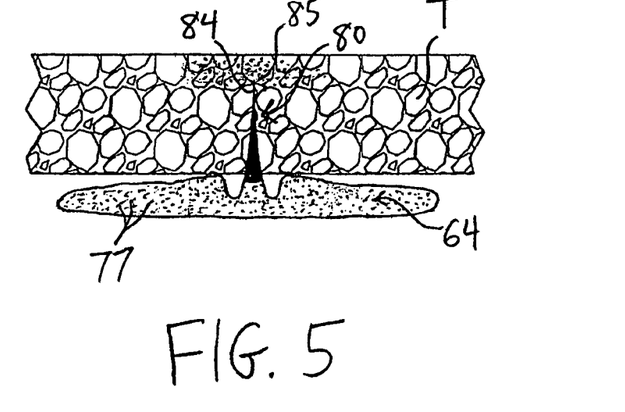

The needles 80 may comprise a suitable material and shape configured to pierce through a target site, such as tissue of a vessel wall or duct, a stenosis, and the like. In one embodiment, the needles 80 may comprise stainless steel. In one embodiment, each needle 80 may comprise a proximal end 82 that is coupled to an associated pocket 64, as shown in FIGS. 3-5. The proximal end 82 of each needle 80 may be coupled to an associated pocket 64 using a suitable technique including, but not limited to, mechanical or adhesion techniques.

Each needle 80 preferably comprises a distally-oriented taper 83, which transitions into a narrower distal end 84 that is configured to pierce through tissue, as shown in FIGS. 3-5. The distal end 84 further comprises a relatively narrow opening 85. A hollow interior space 86 of the needle 80 permits fluid communication between the pocket 64 and the opening 85 of the needle 80, as explained further in FIGS. 3-5 below.

The relatively narrow opening 85 of each needle 80 preferably is sized to permit dispersal of a therapeutic agent when a predetermined pressure threshold is exceeded, i.e., the therapeutic agent preferably must be forced through the relatively narrow opening 85. The predetermined pressure threshold to disperse the therapeutic agent may be exceeded when a sufficient amount of the therapeutic agent has been injected into the confines of each pocket 64, i.e., the pocket 64 reaches maximum expansion from injection of the therapeutic agent, and any additional therapeutic agent injected is forced to flow through the opening 85. In addition, or as an alternative, inflation of the inner balloon member 50 may provide a radially outward force sufficient to urge the therapeutic agent in an outward direction from the pocket 64 through the needle 80, as explained in greater detail below.

As shown in FIG. 2, the apparatus 20 may be used to achieve a biological effect by deploying the needles 80 into engagement with target tissue T. In a first step, a wire guide may be advanced distally towards a target site in a vessel or duct. The apparatus 20 then may be advanced over the wire guide in a contracted delivery configuration to the target site via a wire guide lumen, which may be disposed through the inner cannula 30, i.e., extending adjacent to the inflation lumen 32 and through the distal end 34 of the inner cannula 30.

In the delivery configuration, the inner balloon member 50 is uninflated. An outer sheath may cover the entire apparatus 20 during delivery towards the target tissue T to reduce the likelihood of the needles 80 inadvertently piercing tissue. The apparatus 20, and in particular the needles 80, then may be aligned at a desired location, optionally with the assistance of the radiopaque markers 72 and 74. Upon proper alignment, the outer sheath may be retracted to expose the outer balloon member 60 and the needles 80.

In one exemplary technique, an inflation fluid, such as saline, is then delivered through the inflation lumen 32, through the one or more ports 54, and into the interior space 57 of the inner balloon member 50. Inflation of the inner balloon member 50 may cause the needles 80 to pierce into the target tissue T, as depicted in FIG. 2. At this time, a therapeutic agent 77 may be delivered through the delivery channel 42 and towards the pockets 64 on the outer balloon member 60, as shown in FIG. 2. As the therapeutic agent 77 is delivered, it may fill the pockets 64. Once a sufficient amount of the therapeutic agent 77 has been injected into the confines of each pocket 64, the predetermined pressure threshold noted above may be exceeded to disperse the therapeutic agent 77 through the opening 85 of each needle 80 and into the target tissue T, as depicted in FIG. 2.

In another technique, at least a portion of the therapeutic agent 77 may be delivered through the delivery channel 42 prior to complete inflation of the inner balloon member 50. In this exemplary technique, the inner balloon member 50 may be uninflated or partially inflated, and the therapeutic agent 77 may be delivered through the delivery channel 42 to collect into the pockets 64, without a force sufficient to entirely disperse the therapeutic agent 77 through the needles 80. Subsequently, further expansion of the inner balloon member 50 to a fully expanded state may facilitate the dispersal of the therapeutic agent 77 through the openings 85 of the needles 80 by applying a radially-outward pressure upon the pocket 64 and the therapeutic agent 77 disposed therein.

Upon completion of the procedure using either of the above-referenced techniques, the inner balloon member 50 may be deflated, and the outer sheath may be advanced distally to cover the needles 80. The apparatus 20 then may be proximally retracted and removed from the patient's body.

Advantageously, the apparatus and methods described above permit localized delivery of a therapeutic agent to treat a medical condition, such as a stenosis or an aneurysm. Further, when used to treat conditions such as stenoses, a two-pronged treatment approach is provided whereby the inflation of the inner balloon member 50 may facilitate dilation of the stenosis while therapeutic agents are locally delivered to the stenosis through the needles 80.

The therapeutic agents used in conjunction with the apparatus 20, and any of the other apparatuses described below, may be chosen to perform a desired function upon ejection from the needles 80, and may be tailored for use based on the particular medical application. For example, the therapeutic agent can be selected to treat indications such as coronary artery angioplasty, renal artery angioplasty, carotid artery surgery, renal dialysis fistulae stenosis, or vascular graft stenosis. The therapeutic agent may be delivered in any suitable manner and in any suitable medium. The therapeutic agent may be selected to perform one or more desired biological functions, for example, promoting the ingrowth of tissue from the interior wall of a body vessel, or alternatively, to mitigate or prevent undesired conditions in the vessel wall, such as restenosis. Many other types of therapeutic agents may be used in conjunction with the apparatus 20.

The therapeutic agent employed also may comprise an antithrombogenic bioactive agent, e.g., any bioactive agent that inhibits or prevents thrombus formation within a body vessel. Types of antithrombotic bioactive agents include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid in dissolution of a thrombus.

Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Additionally, or alternatively, the therapeutic agents may include thrombolytic agents used to dissolve blood clots that may adversely affect blood flow in body vessels. A thrombolytic agent is any therapeutic agent that either digests fibrin fibres directly or activates the natural mechanisms for doing so. Examples of commercial thrombolytics, with the corresponding active agent in parenthesis, include, but are not limited to, Abbokinase (urokinase), Abbokinase Open-Cath (urokinase), Activase (alteplase, recombinant), Eminase (anitstreplase), Retavase (reteplase, recombinant), and Streptase (streptokinase). Other commonly used names are anisoylated plasminogen-streptokinase activator complex; APSAC; tissue-type plasminogen activator (recombinant); t-PA; rt-PA. While a few exemplary therapeutic agents have been listed, it will be apparent that numerous other suitable therapeutic agents may be used in conjunction with the apparatus 20 and delivered through the plurality of needles 80 to perform various biological functions.

Referring to FIGS. 3-5, further features of an exemplary pocket 64 and an associated needle 80 are shown. Each of the plurality of pockets 64 may comprise a delivery configuration and an injection configuration. In FIG. 3, the delivery configuration of the pocket 64 and associated needle 80 is shown. The pocket 64 comprises a recess 65 for receiving at least a portion of and preferably the whole of the needle 80. Preferably, the recess 65 is disposed substantially near the center of the pocket 64. The recess 65 may comprise a taper 66, which allows an outer portion of the pocket 64 to be disposed relatively further away from the distal end 84 of the needle 80, as shown in FIG. 3. If the distal end 84 of the needle 80 becomes off-center, then the taper 83 of the needle 80 will substantially cooperate with the taper 66 of the pocket 64. Preferably, the distal end 84 of the needle 80 will be disposed just distal to the pocket 64 at all times (to be within the perimeter of the pocket 64) to reduce or eliminate inadvertent piercing of the pocket 64. Moreover, since the needle 80 may be disposed substantially within the recess 65 of the pocket 64 during delivery, a protective outer sheath may be longitudinally advanced over the needle 80.

In FIG. 4, expansion of the inner balloon member 50 applies a radially outward pressure upon the pocket 64, thereby causing at least partial eversion of the recess 65 and further radial projection of the needle 80. At this time, the distal end 80 of the needle may pierce the target tissue T. In FIG. 5, further expansion of the inner balloon member 50 to a fully expanded state may facilitate the dispersal of the therapeutic agent 77 through the opening 85 of the needle 80 by applying additional pressure upon the pocket 64 and the therapeutic agent 77 in a radially outward direction.

Figure 6:
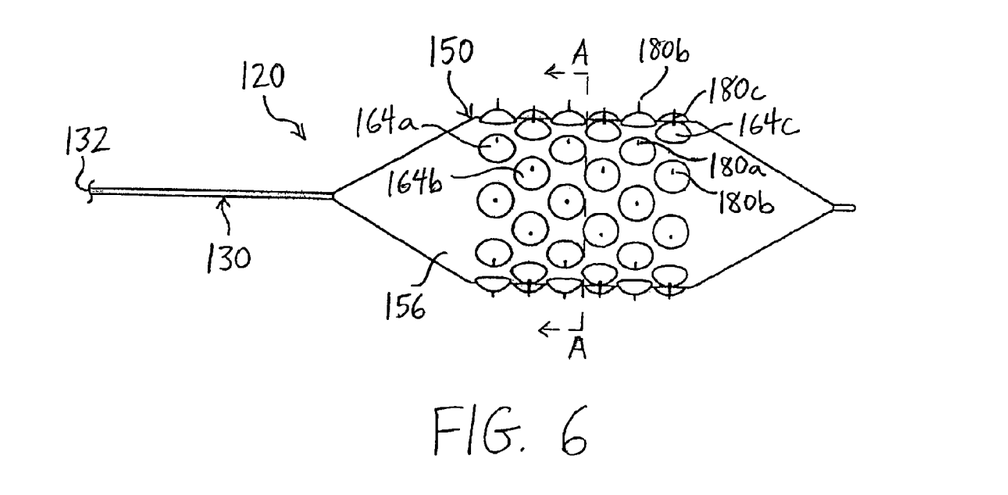
FIG. 6 is a side view of another embodiment of apparatus for delivering at least one therapeutic agent.
Figure 7:
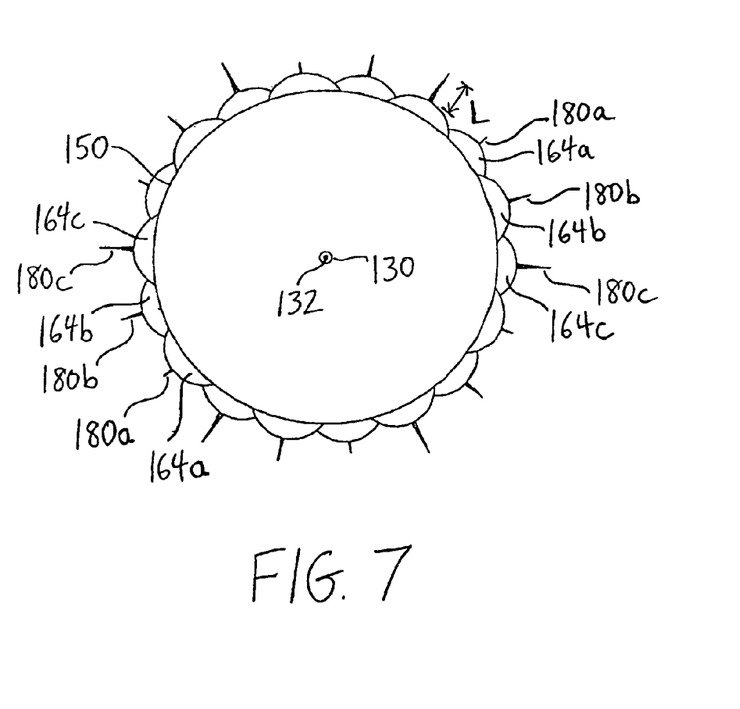
FIG. 7 is a cross-sectional view along line A-A of FIG. 6.

Referring now to FIGS. 6-7, another embodiment of apparatus 120 for delivering one or more therapeutic agents comprises a catheter 130 having a plurality of discrete pockets 164. The discrete pockets 164 are similar to the pockets 64 of FIGS. 1-2. However, in this example, a single balloon member 150 may be used, and each discrete pocket 164 may be coupled directly to an exterior surface 156 of the balloon member 150, or formed integrally with the balloon, without being placed in fluid communication with other pockets 164.

The discrete pockets 164 may be affixed to the exterior surface 156 of the balloon member 150 via adhesive or other suitable means. A therapeutic agent is held in each discrete pocket 164, and a needle 180 is associated with each discrete pocket 164, as shown in FIGS. 6-7. The needles 180 preferably are similar to the needles 80 of FIGS. 3-5, and preferably are deployed in a similar manner.

The therapeutic agent held within each pocket 164 may be dispersed through the distal opening of each needle 180 upon inflation of the balloon member 150. More specifically, inflation of the balloon member 150 imposes a radially-outward pressure upon the pockets 164 and the therapeutic agent sufficient to disperse the therapeutic agent through the needles 180.

In the embodiment of FIGS. 6-7, various pockets 164a-164c may comprise associated needles 180a-180c having different lengths L, as measured from the proximal tip to the distal tip of the needle. In the illustrative example, each needle 180c comprises a first length, which is larger than a second length of each needle 180b, which in turn is larger than a third length of each needle 180a, as depicted in FIGS. 6-7.

Advantageously, the different needles 180a-180c may pierce tissue T at different depths, i.e., based on the individual lengths L of the needles 180a-180c. This may help optimize delivery of one or more therapeutic agents to different depths within tissue. For example, the distal end 84 of each needle 180a may be disposed substantially within an intimal layer, the distal end 84 of each needle 180b may be disposed substantially within a medial layer, and the distal end 84 of each needle 180c may be disposed substantially within an adventitial layer of tissue. Accordingly, one or more therapeutic agents may be delivered to multiple layers of tissue upon deployment of the balloon member 150.

As another advantage, the provision of multiple discrete pockets 164a-164c having needles 180a-180c of different lengths may permit the injection of different therapeutic agents to different tissue regions. For example, a first therapeutic agent may be disposed in each pocket 164a, while second and third therapeutic agents may be disposed in each pocket 164b and 164c, respectively. Upon inflation of the balloon member 150, the first, second and third therapeutic agents are delivered through their respective needles 180a-180c into different layers of a patient's tissue. Accordingly, the use of multiple needles 180a-180c, tied to multiple therapeutic agents and tailored for different layers of the anatomy, allows numerous injections to be consolidated into a single procedure.

For example, in an endovascular application, different cell populations may be delivered to different depths of the vessel wall. In one example, fibroblasts (collagen producing cells) may be delivered to the tunica adventitia, smooth muscle cells (elastin maintenance cells) may be delivered to the tunica media, and endothelial cells (lumen lining cells) may be delivered to the tunica intima. The balloon member 150 also can deliver site-specific appropriate growth factors or soluble matrix proteins to the different layers of a vessel wall. These therapeutic agents could assist in the regulation of the cell populations in the targeted layers of the vessel wall or assist in the acute stabilization of the extracellular matrix.

In one example, where the device is used to deliver a therapeutic agent into an aortic or peripheral artery, an individual lengths L of the needle 180a may be about 0.1 to 1.0 mm in length with an orifice diameter of about 50 to 1000 μm to deliver a therapeutic agent or cells to the tunica intima. An individual lengths L of the needle 180b may be about 1.0 to 3.5 mm in length with an orifice diameter of about 50 to 1000 μm to deliver a therapeutic agent or cells to the tunica media, and an individual lengths L of the needle 180c may be about 3.5 to 5.0 mm in length with an orifice diameter of about 50 to 1000 μm to deliver a therapeutic agent or cells to the tunica adventitia. If there is thrombus formation along an inner wall of the vessel, then the needle length may be dimensioned to account for the estimated thickness of the thrombus, in addition to the dimensions stated above. It should be noted that such dimensions are provided for exemplary purposes only and are not intended to be limiting.

As a further example, the apparatus 120 may be used for intra-urethral or intra-rectal injections of cells into the sphincter of either location at multiple depths simultaneously. This would permit a single procedure and injection that would deliver cells to multiple depths of the tissue, thereby providing increased exposure of the entire sphincter to the new cell population.

Still further applications of the apparatus 120 are possible. Moreover, it will be appreciated the while three different needles lengths have been discussed, greater or fewer needle lengths may be provided. Further, greater or fewer than three therapeutic agents may be provided, and multiple different therapeutic agents may be delivered into the same layer of tissue.

Referring now to FIGS. 8-10, another embodiment is disclosed for delivering at least one therapeutic agent. Like the embodiment of FIGS. 6-7, apparatus 220 comprises needles 280a-280c having different lengths, which may be used to deliver one or more therapeutic agents to different layers of tissue. One main difference regarding FIGS. 8-10 is that a first series of pockets 264a are in fluid communication with one another to deliver a first therapeutic agent, a second series of pockets 264b are in fluid communication with one another to deliver a second therapeutic agent, and a third series of pockets 264 are in fluid communication with one another to deliver a third therapeutic agent.

In FIG. 8, the apparatus 220 comprises a catheter 230 having proximal and distal regions and a balloon member 250 coupled to the distal region of the catheter 230. The catheter 230 may comprise an inflation lumen 232 and first, second and third delivery channels 242a-242c, respectively, as shown in FIG. 9. The inflation lumen 232 and the delivery channels 242a-242c may be integrally formed with the catheter 230, e.g., by extrusion. Alternatively, separate inflation and delivery channels may be provided using one or more additional pieces of tubing disposed on an external surface of the catheter 230.

The first series of pockets 264a may be placed in fluid communication with each other, and with the first delivery channel 242a of the catheter 230, via a series of balloon channels 262a, as shown in FIG. 8. The balloon channels 262a may be formed by attaching a thin layer of balloon material, or another suitable material, over the main balloon member 250. Lateral edges of the balloon channels 262a then may be adhered to the outer surface of the balloon member 250, while a central channel of the balloon channel 262a is not adhered to the balloon member 250 to provide a pathway for fluid flow on the outside of the balloon member 250. In a similar manner, a series of balloon channels 262b may be used to provide fluid communication between the second series of pockets 264b and the second delivery channel 242b, while a series of balloon channels 262c may be used to provide fluid communication between the third series of pockets 264c and the third delivery channel 242c, as shown in FIG. 8.

A proximal region of the catheter 230 may be coupled to a proximal assembly 270 via a coupling member 276, as shown in FIG. 10. The proximal assembly 270 may comprise a first port 271, which is in fluid communication with the inflation lumen 232, and additional ports 272a-272c, which are in fluid communication with the delivery channels 242a-242c, respectively. A coupling member 277 may be disposed between the main body of the catheter 230 and the balloon member 250 to facilitate direction of flow from the delivery channels 242a-242c into their respective balloon channels 262a-262c.

In use, after the needles 280a-280c have been advanced and positioned adjacent to a target site, the balloon member 250 may be inflated by providing an inflation fluid, such as saline, through the first port 271 and the inflation lumen 232. Upon inflation of the balloon member 250, the needles 280a-280c may engage tissue. Since the needles 280a-280c comprise different lengths, as described above, they may extend into different depths of the tissue at the target site.

A first therapeutic agent then may be delivered through the port 272a, through the delivery channel 242a and the balloon channels 262a and into the associated pockets 264a, then dispersed through the associated needles 280a to a first depth in the tissue. Similarly, a second therapeutic agent then may be delivered through the port 272b, through the delivery channel 242b and the balloon channels 262b, and into the associated pockets 264b, then dispersed through the associated needles 280b to a second depth in the tissue. Finally, a third therapeutic agent then may be delivered through the port 272c, through the delivery channel 242c and the balloon channels 262c, and into the associated pockets 264c, then dispersed through the associated needles 280c to a third depth in the tissue.

Optionally, the balloon member 250 then may be deflated, a sheath may be advanced to cover the needles 280a-280c, and the catheter 230 may be rotated circumferentially, e.g., 90 or 180 degrees, to align the different needles with different circumferential sections of the tissue. The sheath then may be retracted, the balloon member 250 re-inflated, and the therapeutic agents then are delivered to a new region within the tissue.

Figure 11:
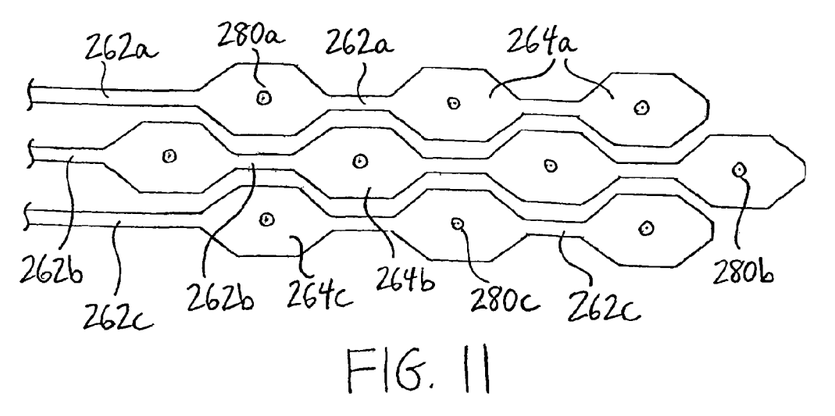
FIG. 11 is a schematic view of an exemplary arrangement of multiple pockets and needles.

Referring to FIG. 11, the balloon channels 262a-262c, the pockets 264a-264c and the needles 280a-280c are arranged in a slightly different manner than shown in FIGS. 8-10. In FIG. 11, the balloon channels 262a-262c, the pockets 264a-264c and the needles 280a-280c are disposed in substantially closer proximity around the perimeter of the balloon member 250. In this example, substantially hexagonal shaped pockets 264a-264c are provided. The pockets 264a of a first row are offset with the pockets 264b of an adjacent row, which in turn are offset from the pockets 264c of a third row, thereby allowing adjacent balloon channels 262a-262c and pockets 264a-264c to be nestled together, as shown in FIG. 11.

In the embodiment of FIG. 11, first, second and third therapeutic agents may be delivered through the needles 280a-280c, respectively. The different therapeutic agents are injected at nearly the same tissue location, since the pockets 264a-264c and associated needles 280a-280c are nestled together, but the different therapeutic agents may be injected at different tissue depths since the different needles 280a-280c may comprise different lengths, as noted above. After injection of the different therapeutic agents to different depths in the tissue, the balloon member 250 may be deflated, a sheath may be advanced to cover the needles 280a-280c, and the catheter may be rotated circumferentially, e.g., 90 or 180 degrees, to align the needles 280a-280c with different circumferential sections of the tissue. The sheath then may be retracted, the balloon re-inflated, and the therapeutic agents then are delivered to a new region within the tissue.

Figure 12:
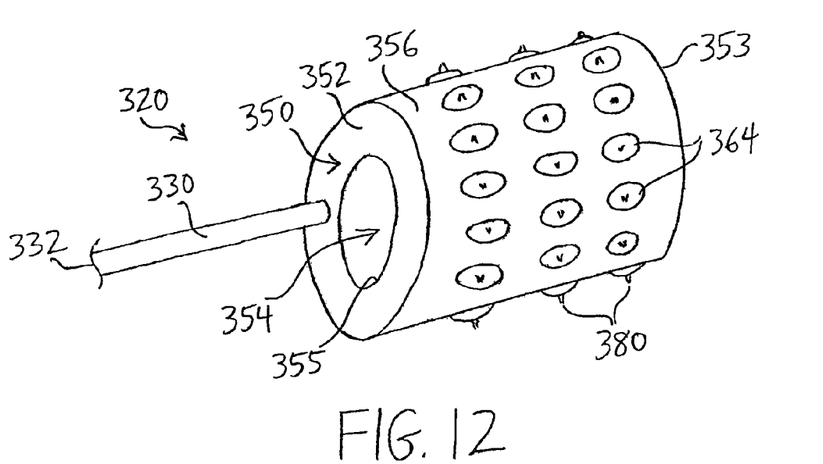
FIG. 12 is a perspective view of another embodiment of apparatus for delivering at least one therapeutic agent.
Figure 13:
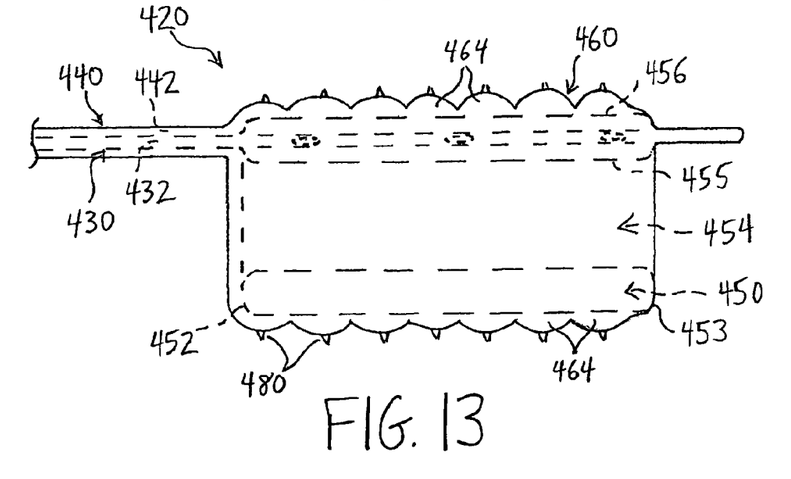
FIG. 13 is a side view of another embodiment of apparatus for delivering at least one therapeutic agent.

Referring now to FIGS. 12-13, in some embodiments, a balloon member comprises a central lumen configured to allow uninterrupted blood flow during the delivery of one or more therapeutic agents according to the techniques described above. In FIG. 12, apparatus 320 comprises a catheter 330 having an inflation lumen 332, and further comprises a toroidally-shaped balloon member 350 having a first end 352, a second end 353, an inner surface 355 and an outer surface 356. In the inflated state of FIG. 12, a central lumen 354 is formed within the inner surface 355 and between the first and seconds ends 352 and 353.

A plurality of discrete pockets 364 having associated needles 380 are disposed on the outer surface 356 of the balloon member 350, and preferably are provided in accordance with the discrete pockets 164a-164c and the needles 180a-180c of FIGS. 6-7 above. When the balloon member 350 is inflated via the inflation lumen 332, the needles 380 may penetrate into tissue a predetermined depth and dispense one or more therapeutic agents, as set forth in FIGS. 6-7 above. Moreover, the central lumen 354 permits blood flow within the vessel or duct while the balloon member 350 is inflated and the therapeutic agents are dispensed.

In FIG. 13, apparatus 420 comprises an inner cannula 430 having an inflation lumen 432 and an outer cannula 440 forming a delivery channel 442 therein. The inner and outer cannulas 430 and 440 may be provided generally in accordance with the inner and outer cannulas 30 and 40, respectively, as described in FIG. 1 above. The apparatus 420 further comprises a toroidally-shaped inner balloon member 450, which is similar to the balloon member 350 of FIG. 12. The inner balloon member 450 comprises a first end 452, a second end 453, an inner surface 455 and an outer surface 456. In an inflated state, a central lumen 454 is formed within the inner surface 455 and between the first and seconds ends 452 and 453, as depicted in FIG. 13.

A plurality of interconnected pockets 464 having associated needles 480 are disposed on an outer balloon member 460, which preferably is similar to the outer balloon member 60 of FIG. 1. In use, the inner balloon member 450 is inflated via the inflation lumen 432, and then a therapeutic agent may be delivered through the channel 442, the pockets 464 and the associated needles 480, thereby dispensing the therapeutic agent into the tissue as set forth above. Moreover, the central lumen 454 permits blood flow within the vessel or duct while the balloon member 450 is inflated and the therapeutic agents are dispensed.

While various embodiments of the invention have been described, it will be apparent to those of ordinary skill in the art that many more embodiments and implementations are possible within the scope of the invention. In this regard, the various features of the described embodiments can be incorporated into the other described embodiments, singly or in combination. Moreover, the advantages described herein are not necessarily the only advantages of the invention and it is not necessarily expected that every embodiment of the invention will achieve all of the advantages described.

The disclosures in U.S. patent application No. 61/091,894, from which this application claims priority, and in the abstract accompanying this application are incorporated herein by reference.

The invention claimed is:

1. An apparatus for treating tissue at a target site, the apparatus comprising:
   a catheter having proximal and distal regions;
   a balloon member disposed on the distal region of the catheter, the balloon having uninflated and inflated states;
   a plurality of pockets on a surface of the balloon member, wherein each of the plurality of pockets comprises a recess having a taper for receiving at least a portion of a needle; and
   a plurality of needles, wherein each of the plurality of needles comprises a taper, and wherein at least one needle is associated with at least one of the plurality of pockets and in fluid communication with the associated pocket,
   where the plurality of needles are operable to engage tissue when the balloon is in the inflated state, and each of the plurality of needles comprises openings sized to disperse a therapeutic agent from an associated pocket into the tissue when the balloon is in the inflated state, and
   where a first needle of the plurality of needles comprises a first length and a second needle comprises a second length different from the first length.

2. The apparatus of claim 1 where each of the plurality of pockets is separate and discrete from another pocket, and where a therapeutic agent is disposed individually within each of the plurality of pockets.

3. The apparatus of claim 1 where each of the plurality of pockets is in fluid communication with at least one other pocket.

4. The apparatus of claim 1 where each of the plurality of pockets comprises a delivery configuration in which the recess is configured to receive a portion of an associated needle, and further comprises an injection configuration where the recess is at least partially everted and the associated needle projects radially outward.

5. The apparatus of claim 1 where the first and second needles of the plurality of needles each comprise a proximal end that is coupled to an associated pocket, a distally-oriented taper, and a distal end that is configured to engage tissue,
   where the distal end of the first needle extends a further depth into tissue, relative to the distal end of the second needle, when the balloon is in the inflated state.

6. The apparatus of claim 5 further comprising:
   a first therapeutic agent adapted to be delivered through the first needle; and
   a second therapeutic agent, different than the first therapeutic agent, adapted to be delivered through the second needle,
   where the first therapeutic agent is delivered to a further depth into the tissue, relative to the second therapeutic agent, when the balloon is in the inflated state.

7. The apparatus of claim 6 where a first series of pockets comprising needles having first lengths are in fluid communication with one another, and a second series of pockets comprising needles having second lengths are in fluid communication with one another,
   where the needles having the first lengths are configured to deliver a first therapeutic agent from the first series of pockets to a first depth in the tissue; and
   where the needles having the second lengths are configured to deliver a second therapeutic agent from the first series of pockets to a second depth in the tissue.

8. The apparatus of claim 1 where the balloon member comprises a central lumen configured to permit blood flow therethrough when the balloon is in the inflated state.

9. A method for treating tissue at a target site, the method comprising:
   providing a catheter having proximal and distal regions and a balloon member disposed on the distal region of the catheter;
   providing a plurality of pockets on a surface of the balloon member, and at least one needle associated with at least one of the plurality of pockets;
   advancing the catheter to a target site with the balloon member in the uninflated state;
   inflating the balloon member to cause the plurality of needles to engage tissue;
   dispersing a first therapeutic agent from a first pocket into the tissue, via a first needle, when the balloon is in the inflated state; and
   dispersing a second therapeutic agent from a second pocket into the tissue, via a second needle, when the balloon is in the inflated state,
   where the first needle comprises a first length that is greater than a second length of the second needle to deliver the first therapeutic agent to a further depth into the tissue, relative to the second therapeutic agent, and
   where the second pocket is discrete from the first pocket.

10. The method of claim 9 where each of the plurality of pockets is separate and discrete from another pocket.

11. The method of claim 9 where each of the plurality of pockets is in fluid communication with at least one other pocket.

12. The method of claim 9 further comprising:
    advancing the catheter to a target site with each of the plurality of pockets in a delivery configuration whereby each pocket comprises a recess for receiving an associated needle; and
    inflating the balloon to at least partially evert the recess and cause the associated needle to project radially outward.

13. The method of claim 9 where a first series of pockets comprising needles having first lengths are in fluid communication with one another, and a second series of pockets comprising needles having second lengths are in fluid communication with one another, the method further comprising:
    delivering a first therapeutic agent through the first series of pockets to a first depth in the tissue via the needles having the first lengths; and
    delivering a second therapeutic agent through the second series of pockets to a second depth in the tissue via the needles having the second lengths.

14. The method of claim 9 further comprising:
    providing a central lumen within the balloon member; and
    permitting blood to flow through the central lumen when the balloon member is in the inflated state.

* * * * *